United States Patent [19]

McDevitt

[11] 4,108,003
[45] Aug. 22, 1978

[54] DEVICE FOR OBTAINING A SAMPLE OF LIQUID

[76] Inventor: Robert F. McDevitt, P.O. Box 551, Ogden Dunes, Portage, Ind. 46368

[21] Appl. No.: 768,709

[22] Filed: Feb. 15, 1977

Related U.S. Application Data

[60] Division of Ser. No. 720,697, Sep. 7, 1976, which is a continuation of Ser. No. 565,396, Apr. 7, 1975, abandoned.

[51] Int. Cl.$^2$ .............................................. G01N 1/12
[52] U.S. Cl. ............................................. 73/425.4 R
[58] Field of Search .................. 73/DIG. 9, 425.4 R; 164/4; 249/DIG. 4

[56] References Cited

U.S. PATENT DOCUMENTS

| 3,897,689 | 8/1975 | Boron | 73/425.4 R |
| 4,002,074 | 1/1977 | Collins | 73/DIG. 9 |

*Primary Examiner*—S. Clement Swisher

[57] ABSTRACT

The invention involves a device for obtaining a sample of molten metal.

More particularly, the purpose of the invention is to provide a safe and simple method whereby a cast sample for example, may be obtained from a flowing metal stream when molten metal is being transferred by pouring from one type vessel to another. The size and shape of the casting is designed to provide a precision sample, requiring a minimum of preparation, that meets laboratory testing procedures. The sample may be used directly for spectographic analysis or can be drilled to provide a sample for wet chemical analysis.

The entire sample can be cast in a two piece mold assembly or device made of a material with optimum cooling venting and dimensional characteristics. This sample is representative of the material being tested and can be used for either chemical analysis or metallographic examinations.

15 Claims, 5 Drawing Figures

DEVICE FOR OBTAINING A SAMPLE OF LIQUID

The subject application is a division of my application Ser. No. 720,697 filed Sept. 7, 1976 which is a continuation of my earlier application Ser. No. 565,396 filed Apr. 7, 1975, now abandoned.

DESCRIPTION OF THE TESTING PROCEDURE

In the processing of metals in the molten state it is necessary to obtain a sample representative of the parent material, at various stages in the processing, for the evaluation of either its chemical composition or metallographic structure.

The device or sampler embodying the subject invention is preferably designed to obtain a quick chilled sample from the flowing metal as it is transferred by pouring from one type vessel to another. It is primarily designed to be used where molten steel is poured from a teeming ladle into a mold.

The device also has application in the continuous casting process during transfer of molten metal from ladle to tundish to mold under controlled condition. This device has further application in any area or with any molten metal where the molten metal is transferred from one vessel to another under controlled conditions.

For many years the typical method of sampling molten metal in the steel industry was to use what was defined as a spoon. The spoon consisted of a deep bowl type ladle or sampler attached to the end of a long handle and made of either cast or forged steel. The spoon varied in size and had a lip to facilitate pouring. In practice the pouring stream was controlled to a slow or partial stream and the spoon was then dipped into the stream of metal to obtain the sample. The spoon was usually tipped into either the right or left side of the stream, whichever was most convenient, and partially filled with molten metal. The molten metal content of the spoon was then poured into a small test mold positioned on the platform.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is most pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

Advantages of the invention or inventions over the spoon technique are:
1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

OBJECTIVES

In view of the foregoing, one of the important objects of the invention is to provide an elongated device for obtaining a sample of a liquid, such as molten metal, which comprises, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the sections. More particularly in this respect, one of the holding means for the sections comprises clip means, and an appendage held in place by this clip means may be utilized for identificating purposes and effect release of the clip means, and the means for holding the sections and tubular means may be utilized for the same purpose.

A significant object of the invention is to provide a device of the character described above in which each section includes a relatively large head portion provided with a recess and an extended portion having a center groove therein so that when the sections are correctly assembled the recesses will form a primary chamber and the grooved extensions will form a tubular formation communicating with the chamber.

Also, an object of the invention is to provide a device as described in the preceding paragraph in which the extended portions adjacent the head portions of the sections are provided with mating grooves or seats and the means for holding the extended portions together may comprise a split resiliently flexible ring engaging the seats or a sleeve surrounding the extended portions having a portion indented into the seats.

Additional objects and advantages of the invention reside in providing a device which is safe and efficient to use, durable and comprised of components which can be economically manufactured and assembled on a production basis.

Other objects and advantages will become apparent after the description hereinafter set forth is considered in conjunction with the drawings annexed hereto.

DRAWINGS

DESCRIPTION

Figure 1:
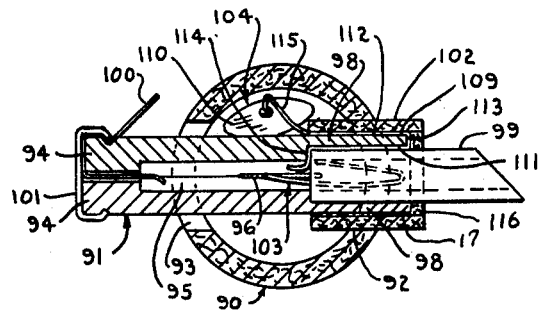
FIG. 1 is a sectional view of a device embodying the invention.
Figure 2:
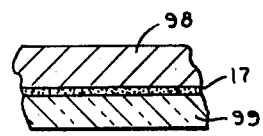
FIG. 2 is an enlarged partial section showing a mode of securing together certain components of the device.

FIG. 1 discloses a connector generally designated 90 and a device generally designated 91. The connector is provided with a pair of aligned round side openings 92 and 93 of different diameters disposed on a line transverse to the longitudinal axis of the connector.

Figure 4:
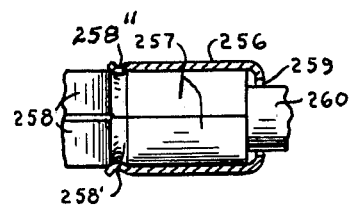
FIG. 4 is a view, partially in section of a modified way of securing half sections of a device together.

The device 91 is quite similar to the device shown in FIG. 12 of my copending application and comprises a pair of recessed half sections 94 constructed to provide a chamber 95 and side vents 96 like the vent 18 shown in FIGS. 4 and 12 of that application. These half sections also include channel portions 98 which form a tubular formation for receiving an inner extremity of a tubular means 99. The device also includes an appendage 100, clip means 101, and a sleeve 102, like those described above including a metal deoxidizing element generally designated 103 and what may be termed a trigger or manipulative assembly generally designated 104.

Figure 3:
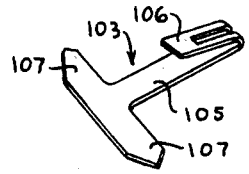
FIG. 3 is a perspective view of a deoxidizing element utilized in the device.

The deoxidizing element 103 may be designed and constructed as desired but is preferably generally T-shaped or articulated as exemplified in FIG. 3 and includes a stem 105 having a slotted continuation 106 bent back at an acute angle over the stem and a pair of opposed portions 107 constituting the cross of the T. This element is secured in place by locating remote ends of the portions 107 in the vents and the stem 105 and its continuation 106 in the tubular means 99 so as to insure the inflow of metal will be thoroughly subjected to conditioning by the deoxidizing means both in the tubular means and chamber. The continuation 106 due to its slotted character serves to expedite melting thereof and conditioning of the metal. The free ends of the portions 107 of the element are preferably bevelled or pointed to some extent for disposition in side openings or vents 96 formed by the notches in the head portions so that some metal may flow outwardly through the vents to provide laterally extending arcuate portions 108 of a sample such as depicted in FIG. 22 of said continuation application.

The trigger assembly generally designated 104 is unique and preferably includes a generally U-shaped metal member 109 and a disc-like handle 110. The member has a leg 111 located between one of the portions 98 of the head sections and the tubular means 99 and a leg portion 112 between the portion 98 and the sleeve 102, a bridge portion 113 engaging an end of the portion 98, an offset inner end portion 114 extending into the chamber 95 and an outer offset end 115 to which is connected the handle 110 or a tag. This trigger assembly affords a setup whereby after a sample has been obtained, the handle or tag can be pulled in the appropriate direction or directions whereby to assist in separating the sleeve 102 from the half sections and tubular means. It should be noted that means, such as cement or a washer 116 of pasteboard is preferably secured in the outer end of the sleeve and about the tubular means to provide a seal therebetween. It should also be noted that the side opening 92 above referred to, has a diameter to facilitate entry of the sleeve 102 of the device and that the opening 93 is larger than the opening 92 and accommodates the head or larger extremity of the device. It should be further noted that the device may be rotated about its axis relative to the connector to any position desired by an operator to facilitate entry of the tubular means into the molten metal. The tubular means 99 may be secured in place in the tubular formation formed by the channel portions 98 by the cement or as alluded to above and cement 17 may be used to secure the sleeve about the channel portions 98.

FIG. 4 shows means in the form of a tubular fitting or fastener 256 whereby extended portions 257 of a pair of half sections 258 may be secured together in a mode different from the sleeve 102 above referred to. The extended portions are preferably provided with matching grooves 258' or seats and the fitting or fastener is preferably in the form of a metal ferrule comprising a cylindrical portion surrounding the portions 257 and an end wall provided with an opening 259 through which a tubular means 260 extends. An inner portion of the sleeve is preferably deformed or indented into the grooves 258' for locking or holding the sections together.

Figure 5:
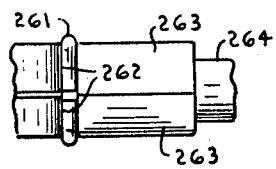
FIG. 5 is a partial view showing a different mode of securing half sections together.

FIG. 5 is a view similar to FIG. 4 showing a different form of a fastener 261 comprising a split round flexible ring which is adapted to be manually flexed into mating grooves 262 provided in extended portions 263 of a pair of half sections for securing the sections together about a tubular means 264.

In view of the foregoing it will be manifest that the means 104, 256 and 261 afford various unique ways of holding the sections assembled and that they may for example, be applied to the devices shown in FIGS. 12 and 17 of said copending application as is evident therefrom. It is also apparent that the clip means 101 and fastener 261 are of a resiliently flexible or expansible-contractible character and facilitate assembly and disassembly of the sections 94.

Elucidating further with respect to the use of the device in obtaining a sample, the sampling device is attached to the end of the lance or wand 4 as shown in FIG. 1 of said continuation application, so that the feed tube of the device is perpendicular to the axis of the lance. The individual taking the sample grasps the lance, faces the stream of molten metal, and holds the lance such that the feed tube of the device is near and parallel to the flow of the metal stream, twists the assembly or device so the open end of the feed tube is inserted into the flow of the molten metal. The opening of the tube should be held at an angle to permit an unrestricted flow of the metal down the inside of the tube into the interior of the device. The open end of the tube is inserted just inside the outer surface of the stream to utilize the full volumetric capacity of the feed tube and minimize exposure of the incoming metal to the atmosphere.

As the sampling time using the invention is short, the sample size small and the mold enclosed, exposure to the atmosphere is greatly reduced, therefore reaction of the molten metal with oxygen is limited. Another important factor is the rapid transformation accelerated by the mold design and the material employed. Rapid solidification minimizes chemical segregation and promotes a uniform structure.

It is theorized that when a molten metal sample is taken using powdered metal molds the sample is transformed quickly from the liquid to solid state by the combined action of the emissivity of the surface which allows the sintered iron mold to absorb the heat rapidly and the good conductivity of the iron allows the heat to transfer throughout the mass of the mold by conduction and convection. The good radiation characteristics of the outer surface allows for dissipation of the heat to the atmosphere. The quick chill effect of the mold design of the device coupled with its venting characteristics have permitted the design to incorporate the use of small extensions attached to the primary disc. These extensions are used primarily for the analysis of carbon and sulfur and their globular shape allows uniform cooling and solidification of the molten metal with a minimum of chemical segregation. Analysis of the elements from these samples may compare more favorably with analysis of drillings obtained from the primary disc and also with analysis obtained from product checks and possibly samples severed from glass enclosed pins which may cool differentially and have a tendency to segregate chemically.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device for obtaining a sample of liquid from a supply thereof, said device comprising a pair of elongated half sections, each of said sections being provided with an enlarged portion provided with a recess and a smaller channel portion, first means and second means respectively securing said enlarged portions and said channel portions together whereby said recesses and said channel portions respectively form a chamber and an elongated opening, a tube having an inner extremity secured in said opening and an outer extremity provided with an entrance for a liquid for flow into said chamber via said tube, and manipulatible means having a portion interposed between at least one of said channel portions and said second means whereby to facilitate their separation after a sample is received by the device.

2. The device defined in claim 1, in which said second means securing said channel portions comprises a sleeve which surrounds said channel portions and assists in holding said tube in said opening and said manipulatible means also has a portion interposed between at least one of said channel portions and said tube whereby to facilitate their separation.

3. A device for obtaining a sample of liquid from a supply thereof, said device comprising a pair of half sections, each of said sections having an enlarged portion provided with a recess and a small channel portion, means securing said sections together whereby said recesses and channel portions respectively form a chamber and an elongated opening, and a tube having an inner extremity secured in said elongated opening and an outer extremity provided with means facilitating entry of a liquid into the tube for flow into said chamber, said securing means comprising resiliently flexible structure embracing said channel portions.

4. A subassembly of a device for obtaining a sample of liquid from a supply thereof, said device being elongated and comprising a pair of half sections having head portions forming a chamber and channel portions forming an elongated opening communicating with said chamber, and a pair of expansible-contractible means respectively cooperating with said head portions and said channel portions for holding them assembled in a manner whereby to facilitate their separation.

5. The device defined in claim 4, in which said head portions are provided with mating notches forming openings communicating with said chamber, and a deoxidizing means is disposed in the chamber and has portions which are respectively loosely disposed in said openings.

6. The device defined in claim 4, in which said head portions form a rear opening which communicates with said chamber and is located in axially spaced relation to said elongated opening, and an appendage is held in relation to said head portions by one of said pair of means for disposition in said rear opening and chamber.

7. The device defined in claim 4, in which said head portions form a rear opening which communicates with said chamber and is located in axially spaced relation to said elongated opening, an appendage extends through said rear opening and into said chamber, one of said cooperating means is secured to said head portions and serves to lock the appendage in place, and said appendage may be utilized to assist in the release of this cooperating means from said head portions.

8. A subassembly of a device for obtaining a sample of liquid from a supply thereof, said subassembly being elongated and comprising a pair of half sections, each of said sections comprising a head provided with a recess and a channel extension, and resiliently flexible clip means cooperating with said channel extensions for securing said sections whereby the recesses and extensions respectively form a chamber and an opening.

9. A subassembly for use as a component of a device for obtaining a sample of molten material from a supply thereof, said subassembly comprising a pair of sections forming an enlargement provided with internal surfaces forming a chamber and a reduced tubular formation, a tube having an inner extremity disposed in said tubular formation and an outer end for receiving molten material for flow into said chamber, means for holding said tube in said tubular formation and said sections assembled, and manually operable means extending laterally from at least one of said sections for facilitating release of said tube from said tubular formation and separation of said sections after a sample of molten material has been received in said chamber.

10. A device for obtaining a sample of liquid from a supply thereof, said device including a subassembly comprising a pair of half sections, each of said sections comprising a head provided with a recess and a channel extension, expansible-contractible means for securing said sections whereby the recesses and extensions respectively form a primary chamber and a tubular formation, tubular means having an inner extremity secured in tubular formation and an outer extremity provided with an entrance whereby liquid may be caused to flow through said tubular means into said primary and secondary chamber and said clip means being disposed about said extensions and serving to facilitate separation of said sections and tubular means after the device receives a sample of liquid.

11. A subassembly of a device for obtaining a sample of molten metal, said subassembly comprising a pair of elongated members which when assembled form a chamber for receiving molten metal and a tubular portion through which the metal flows into the chamber, a pair of means respectively embracing portions of the extremities of said members for holding the members assembled, and one of said means about said tubular portion being of a resiliently flexible character.

12. A subassembly of a device for obtaining a sample of liquid from a supply thereof, said subassembly being elongated and comprising a pair of elongated sections forming a chamber at one extremity and an entrance to the chamber at its opposite extremity, and a pair of expansible-contractible means respectively cooperating with said extremities whereby to facilitate assembly and disassembly of said sections.

13. A subassembly of a device for obtaining a sample of liquid from a supply thereof, said subassembly being elongated and comprising a pair of sections forming a chamber at one extremity and an entrance to the chamber at its opposite extremity, and resiliently flexible clip means cooperating with said opposite extremity whereby to facilitate assembly and disassembly of said sections.

14. A subassembly for use as a component of a device for obtaining a sample of molten material from a supply thereof, said subassembly being elongated and comprising a pair of sections forming a chamber at one extremity and an entrance to the chamber at its opposite extremity, said sections at said opposite extremity being provided with seats, and means substantially surrounding said opposite extremity and engaging said seats whereby to assist in holding said sections assembled.

15. The subassembly defined in claim 9, in which said manually operable means includes a handle.

* * * * *